(12) United States Patent
Brito De La Fuente et al.

(10) Patent No.: US 9,801,846 B2
(45) Date of Patent: Oct. 31, 2017

(54) COMPOSITION COMPRISING EPA AND DHA ETHYLESTER FOR PARENTERAL ADMINISTRATION

(71) Applicant: Fresenius Kabi Deutschland GmbH, Bad Homburg (DE)

(72) Inventors: Edmundo Brito De La Fuente, Friedrichsdorf (DE); Crispulo Gallegos-Montes, Bad Homburg (DE); Lida A. Quinchia-Bustamente, Bad Homburg (DE)

(73) Assignee: Fresenius Kabi Deutchland GmbH, Bad Homburg (DE)

( * ) Notice: Subject to any disclaimer, the term of this patent is extended or adjusted under 35 U.S.C. 154(b) by 0 days.

(21) Appl. No.: 15/114,937

(22) PCT Filed: Jan. 28, 2015

(86) PCT No.: PCT/EP2015/051656
§ 371 (c)(1),
(2) Date: Jul. 28, 2016

(87) PCT Pub. No.: WO2015/113986
PCT Pub. Date: Aug. 6, 2015

(65) Prior Publication Data
US 2016/0346242 A1 Dec. 1, 2016

(30) Foreign Application Priority Data

Jan. 28, 2014 (EP) .................................. 14152786

(51) Int. Cl.
*A61K 31/232* (2006.01)
*A61K 9/00* (2006.01)
*A61K 47/12* (2006.01)
*A61K 47/24* (2006.01)
*A61K 9/107* (2006.01)
*A61K 47/10* (2017.01)

(52) U.S. Cl.
CPC .......... *A61K 31/232* (2013.01); *A61K 9/0029* (2013.01); *A61K 9/107* (2013.01); *A61K 47/10* (2013.01); *A61K 47/12* (2013.01); *A61K 47/24* (2013.01)

(58) Field of Classification Search
CPC ..... A61K 31/23; A61K 31/355; A61K 31/375
USPC ........................................ 514/549, 458, 474
See application file for complete search history.

(56) References Cited

U.S. PATENT DOCUMENTS 5,874,470 A  2/1999  Nehne

FOREIGN PATENT DOCUMENTS

EP  2 308 493  4/2011

*Primary Examiner* — Raymond J Henley, III
(74) *Attorney, Agent, or Firm* — Occhiuti & Rohlicek LLP

(57) ABSTRACT

Described herein are compositions for parenteral administration that include an aqueous phase and 5 to 30%, by weight, of an oil phase, based on the total weight of the composition. The oil phase comprises the omega-3 fatty acid ethylesters eicosapentaenoic acid ethylester, docosahexaenoic acid ethylester, and mixtures thereof. The composition further comprises at least one anionic surfactant and at least one amphoteric surfactant, and less than 0.05% by weight of oleic acid, based on the total weight of the composition. Also described is a method for preparing such a composition as well as such compositions for use as a medicament, in particular for use in treating stroke, sepsis, Alzheimer's disease or cancer. Also featured are methods of treating these conditions by parenterally administering a composition to a patient in need thereof and methods of providing parenteral nutrition to such patients by administering to them a composition as described herein.

17 Claims, 1 Drawing Sheet

COMPOSITION COMPRISING EPA AND DHA ETHYLESTER FOR PARENTERAL ADMINISTRATION

CROSS REFERENCE TO RELATED APPLICATIONS

This application is a U.S. national stage application of International Application No. PCT/EP2015/051656, filed on Jan. 28, 2015, which claims priority to European Application No. 14152786.1, filed on Jan. 28, 2014. The contents of these previously filed applications are hereby incorporated by reference herein in their entirety.

The present invention relates to a composition for parenteral administration comprising an aqueous phase and 5 to 30% by weight of an oil phase, based on the total weight of the composition, wherein the oil phase comprises omega-3 fatty acid ethylester selected from the group consisting of eicosapentaenoic acid ethylester, docosahexaenoic acid ethylester and mixtures thereof, and wherein the composition further comprises at least one anionic surfactant and at least one amphoteric surfactant, and wherein the composition comprises less than 0.05% by weight of oleic acid, based on the total weight of the composition. Further, the present invention relates to a method for preparing such a composition as well as to such a composition for use as a medicament, in particular for use in treating stroke, sepsis, Alzheimer's disease or cancer. Furthermore, the present invention relates to a method for treating stroke, sepsis, Alzheimer's disease or cancer comprising parenterally administering such a composition to a patient in need thereof and to a method of providing parenteral nutrition to a patient suffering from at least one disease selected from stroke, sepsis, Alzheimer's disease or cancer, the method comprising administering such a composition to the patient.

Oil-in-water parenteral emulsions have been used clinically for nutritional and medical purposes for several years. Of the various types of oils used, historically soybean oil and safflower were first introduced almost 50 years ago and thus, with these oils the greatest clinical experience exists. These lipids provide a rich source of non-glucose based calories, essential fatty acids, such as omega-6 fatty acids, vitamins E and K and the like. However, their high proportions of omega-6 fatty acids have raised concerns about their administration as the sole lipid source to critically ill patients and patients with compromised immune function such as patients suffering from sepsis or trauma.

High levels of omega-6 fatty acids have been considered to increase production of mediators which have been correlated with immunosuppressive actions such as impaired reticular endothelial system function and inhibition of lymphocytes, macrophages, and neutrophil functions. Furthermore, the high number of double bonds in omega-6 fatty acids makes them prone to lipid peroxidation.

Meanwhile, fish oils, which are rich in long chain omega-3 fatty acids, and their use in enteral and parenteral nutrition have received attention in the scientific literature and industrial area because of their reported positive role in human health. The potential benefits of omega-3 fatty acids in a diet include reduced risk of several diseases including cardiovascular diseases, hypertension, atherosclerosis, inflammatory and autoimmune disorders. The polyunsaturated fatty acids in fish oils, especially eicosapentaenoic acid (EPA) and docosahexaenoic acid (DHA), have been shown to have a positive effect on preventing a variety of human diseases and disorders. In fish oil, DHA and EPA can be present in a mono-, di-, or triglyceridic form.

Some emulsions which comprise fish oils are thus already known in the art:

For example, WO 87/02247 A1 describes a lipid emulsion of fish oils comprising high concentrations of omega-3 fatty acid esters and low concentrations of free fatty acids for intravenous administration for the treatment of thrombotic disease states.

Further, presently, there are a few commercially available parenteral lipid emulsions containing omega-3 fatty acids derived from fish in clinical use in Europe. The first product available on the market was Omegaven™ (Fresenius Kabi), a 10% fish oil-in-water emulsion. The second product, Lipoplus™ (B. Braun), is a physical mixture of oils of medium chain triglycerides or MCT (50%), soybean (40%) and fish oil (10%). The most recent product is SMOFlipid™ (Fresenius Kabi), and is also a physical mixture of oils: soybean oil (30%), MCT oil (30%), olive oil (25%) and fish oil (15%).

However, unrefined fish oils also contain saturated fatty acids as well as other impurities such as sterols, waxes, lipid soluble vitamins, phenols and other constituents. Accordingly, fish oils must be purified prior to consumption. In addition, fish oils are known to degrade during processing and in storage.

Further, in order to obtain the benefits from omega-3 fatty acids present in these fish oils, a high amount of most emulsions described in the art may need to be consumed due to their comparatively low amount of omega-3 fatty acids. This overconsumption however may increase the intake of cholesterol and other saturated fatty acids which may possibly have deleterious health effects.

Thus, emulsions comprising a higher concentration of omega-3 fatty acids when compared to emulsions which comprise fish oil were proposed in the art. Such emulsions with a high amount of omega-3 fatty acids, however, often tend to be unstable.

For example, WO 2011/103512 A1 describes the preparation of an emulsion comprising an emulsifier, a tonicity agent and a docosahexaenoic acid free fatty acid (DHA-FFA) wherein the emulsion is substantially free of eicosapentaenoic acid (EPA) and derivatives thereof. The emulsion is described to be suitable for parenteral administration.

WO 2011/103510 A1 describes emulsions comprising an oil phase comprising a fish oil enriched in docosahexaenoic acid ethylester. These emulsions comprise besides phospholipids sodium oleate as emulsifier as well as 4% by weight of oleic acid within the oil phase.

WO2011/103514 A1 relates to emulsions for parenteral administration comprising an emulsifier, a tonicity agent and about 100 mg/ml to about 300 mg/ml docosahexaenoic acid triglyceride, wherein the emulsion is substantially free of eicosapentaenoic acid and eicosapentaenoic acid derivatives.

WO 2011/133841 A2 describes 20% oil-in-water emulsions, wherein the oil phase comprises at least one omega-3 essential fatty acid selected from a group consisting of alpha-linolenic acid (ALA), eicosapentaenoic acid (EPA), and docosahexaenoic acid (DHA). Further, the oil phase comprises at least one medium chain triglyceride (MCT). Such MCTs are considered to be convenient in order to enhance the stability of such emulsions (see Driscoll D F, Nehne J, Peterss H et al. The influence of medium-chain triglycerides on the stability of all-in-one formulations. *Int J Pharm.* 2002; 240:1-10).

However, due to the presence of MCTs in most of these emulsions, the amount of omega-3 fatty acids in these emulsions is still not very high. Thus, in order to obtain the benefits from omega-3 fatty acids, also a comparatively high amount of these emulsions needs to be administered. Further, some of the described emulsions are not stable enough for in vivo applications.

Thus, there is still the need for stable emulsions with a high concentration of omega-3 fatty acids and optimum bioavailability for parenteral administration.

SUMMARY OF THE INVENTION

The present invention relates to a composition for parenteral administration comprising an aqueous phase and 5 to 30% by weight of an oil phase, based on the total weight of the composition, wherein the oil phase comprises omega-3 fatty acid ethylesters selected from the group consisting of eicosapentaenoic acid ethylester, docosahexaenoic acid ethylester and mixtures thereof, and wherein the composition further comprises at least one anionic surfactant and at least one amphoteric surfactant, and wherein the composition comprises less than 0.05% by weight of oleic acid, based on the total weight of the composition.

Furthermore the present invention relates to a method for preparing a composition for parenteral administration, and to a composition obtained or obtainable by said method, the composition comprising an aqueous phase and 5 to 30% by weight of an oil phase, based on the total weight of the composition, wherein the oil phase comprises omega-3 fatty acid ethylesters selected from the group consisting of eicosapentaenoic acid ethylester, docosahexaenoic acid ethylester and mixtures thereof, and wherein the composition further comprises at least one anionic surfactant and at least one amphoteric surfactant, and wherein the composition comprises less than 0.05% by weight of oleic acid, based on the total weight of the composition, wherein the method comprises:
(a) providing an aqueous phase comprising the at least one amphoteric surfactant and the at least on anionic surfactant,
(b) providing an oil phase comprising omega-3 fatty acid ethylesters selected from the group consisting of eicosapentaenoic acid ethylester, docosahexaenoic acid ethylester and mixtures thereof,
(c) mixing the oil phase according to (b) with the aqueous phase according to (a).

In a further aspect, the present invention relates to a composition as described above, or to a composition obtainable or obtained by the above described method, for use as a medicament, in particular for use in treating stroke, sepsis, Alzheimer's disease or cancer. In a further aspect, the present invention relates to a composition as described above, or to a composition obtainable or obtained by the above described method, for use in providing parenteral nutrition to a patient suffering from at least one disease selected from stroke, sepsis, Alzheimer's disease or cancer.

DETAILED DESCRIPTION

It was found that an emulsion comprising the combination of omega-3 fatty acid ethylester and at least one amphoteric surfactant and at least one anionic surfactant and comprising less than 0.05% by weight of oleic acid based on the total weight of the final composition, is surprisingly stable even with a comparatively high amount of omega-3 fatty acid ethylester within the composition. It is contemplated that with this composition an advantageous decrease in the necessary dosage as compared to, for instance, fish oil or other compositions known in the art is possible, in particular due to the possibility of providing such stable emulsions being highly enriched in eicosapentaenoic acid ethylester and/or docosahexaenoic acid ethylester.

Oil in Water Emulsion

As described above, the composition according to the present invention and the composition obtained or obtainable by the above described method comprises an aqueous phase and 5 to 30% by weight of an oil phase. Preferably, the composition comprises 5 to 30% by weight of an oil phase, more preferably 5 to 25% by weight of an oil phase, more preferably 10 to 20% by weight of an oil phase, more preferably 15 to 20% by weight of an oil phase.

As to the aqueous phase, this phase preferably comprises water in a purity suitable for intravenous administration.

The amount of water is preferably in the range of from 95 to 70% by weight, preferably 90 to 75% by weight, more preferably 85 to 75% by weight.

Preferably, the composition according to the invention is an emulsion, in particular an oil-in-water emulsion.

In case the emulsion is an oil-in-water emulsion, the oil droplets preferably have a mean particle size ($D_{4,3}$) in the range of from 0.1 μm to 0.3 μm, preferably of from 0.15 μm to 0.25 μm, measured with a LS 13 320 Laser Diffraction Particle Size Analyser (Beckman Coulter) according to USP <729>.

DHA and EPA

As defined above, the oil phase comprises omega-3 fatty acid ethylester selected from the group consisting of eicosapentaenoic acid ethylester, docosahexaenoic acid ethylester and mixtures thereof.

The term "eicosapentaenoic acid (EPA) ethylester" as used herein refers to the ethylester of (5Z,8Z,11Z,14Z,17Z)-5,8,11,14,17-icosapentaenoic acid, also known as 20:5(n-3). EPA is a an omega-3 fatty acid with a 20-carbon chain and five cis double bonds; the first double bond is located at the third carbon from the omega end.

The term docosahexaenoic acid (DHA) ethylester as used herein refers to the ethylester of all-cis-docosa-4,7,10,13,16,19-hexa-enoic acid, also known as is 22:6(n-3). DHA is an omega-3 fatty acid that is a primary structural component of the human brain, cerebral cortex, skin, sperm, testicles and retina. Docosahexaenoic acid is a 22-carbon chain with six cis double bonds, the first double bond being located at the third carbon from the omega end.

Preferably, at least 60% by weight of the oil phase, such as of from 60% by weight to 95% by weight of the oil phase, more preferably at least 65% by weight of the oil phase, more preferably at least 70% by weight of the oil phase, more preferably at least 75% by weight of the oil phase, more preferably at least 80% by weight of the oil phase, more preferably of from 85 to 90% by weight of the oil phase, present in the composition according to the invention or in the composition obtained or obtainable by the method as described above consists of eicosapentaenoic acid ethylester, docosahexaenoic acid ethylester or a mixture thereof.

In particular, the oil phase comprises a mixture of eicosapentaenoic acid ethylester and docosahexaenoic acid ethylester, wherein the weight ratio of eicosapentaenoic acid ethylester relative to docosahexaenoic acid ethylester is preferably in the range of from 1:9 to 9:1.

The EPA and DHA ethylester may be obtained by any way known to those skilled in the art.

It is known that docosahexaenoic acid (DHA) and eicosapentaenoic acid (EPA) and the derivatives thereof are contained per se, or in the form of glycerides and in the form of other derivatives, in natural fats and oils, particularly in fats and oils of aquatic animals (e.g., fish, marine mammals, and crustaceans such as krill and other euphausiids), animal tissues (e.g., brain, liver, eyes, etc.) and animal products such as eggs or milk.

Thus, for example, they may be extracted from animal sources including aquatic animals (e.g., fish, marine mammals, and crustaceans such as krill and other euphausiids), animal tissues (e.g., brain, liver, eyes, etc.) and/or animal products such as eggs or milk.

Some methods for the isolation of these docosahexaenoic acid (DHA) and eicosapentaenoic acid (EPA) and their derivatives and their conversion to pure docosahexaenoic acid (DHA) ethylester and eicosapentaenoic acid (EPA) ethylester are described in the art.

Such isolation by purification can be achieved by any means known to those of skill in the art and can include the extraction, e.g. by supercritical fluid extraction, of an oil from an organism which produces DHA and/or EPA and the subsequent purification via chromatographic methods. Alternatively, the oils can be extracted using extraction techniques such as are described in U.S. Pat. No. 6,750,048. Additional extraction and/or purification techniques are taught e.g. in WO2001076715 and WO/2001/076385.

As to the weight ratio of eicosapentaenoic acid ethylester relative to docosahexaenoic acid ethylester, this weight ratio is preferably in the range of from 1:9 to 9:1, such as 1:9, 1:8, 1:7, 1:6, 1:5, 1:4, 1:3, 1:2, 1:1, 2:1, 3:1, 4:1, 5:1, 6:1, 7:1, 8:1 or 9:1.

Medium Chain Fatty Acid Derivatives

Preferably, the oily phase present in the composition, described above, comprises less than 1% by weight, more preferably less than 0.5% by weight, more preferably less than 0.1% by weight, more preferably less than 0.05% by weight, more preferably less than 0.01% by weight, more preferably essentially no, more preferably no, medium chain fatty acid derivatives, wherein this amount refers to the sum of all medium chain fatty acid derivatives present and is based on the total weight of the oil phase. The term "essentially no" in this context refers to an amount <0.01% by weight including 0% by weight.

The term "medium chain fatty acid derivative" as used hereinunder and above refers to fatty acid derivatives, such as mono-, di- or triglycerides (MCT), comprising a medium chain fatty acid or alkyl esters of medium chain fatty acids these fatty acids being 6 to 12 carbon atoms in length. Medium chain fatty acids include but are not limited to caproic acid, caprylic acid, capric acid and lauric acid.

Surprisingly, it has been found that stable compositions may be provided without these medium chain fatty acid derivatives which, due to the fact that MCTs may be omitted, may comprise an even higher amount of EPA derivatives and DHA derivatives. This finding is particularly surprising since the prior art emphasizes that omega-3 fatty acid comprising compositions should contain MCTs to enhance their stability.

Thus, the present invention also relates to a composition as described above, or to a composition obtainable or obtained by the above described method, wherein the oil phase comprises less than 1% by weight, more preferably less than 0.5% by weight, more preferably less than 0.1% by weight, more preferably less than 0.05% by weight, more preferably less than 0.01% by weight, more preferably essentially no, more preferably no, medium chain fatty acid derivatives.

Surfactant

As described above, the composition comprises at least one amphoteric surfactant and at least one anionic surfactant. The term "surfactant" as used within the meaning of the present invention refers to compounds which stabilize the composition by reducing the interfacial tension between the oil phase and the water phase and which typically comprise at least one hydrophobic group (their tail) and at least one hydrophilic group (their head). These surfactants (which may also be referred to as emulsifiers) are preferably used in amounts effective to provide, optionally together with further surfactants present, stable and even distribution of the oil phase within the aqueous phase. In particular, these surfactants are selected from surfactants which have been approved for parenteral administration.

The Anionic Surfactant

The term "anionic surfactant" refers to surfactants which may ionize in aqueous solution, and in which at neutral pH or higher pH, the hydrophilic group is negatively charged.

In this context, in particular, salts of fatty acids may be mentioned, such as e.g. sodium oleate, potassium oleate, sodium stearate and/or sodium deoxycholate. Thus, preferably, the at least one anionic surfactant is a salt of a fatty acid, more preferably selected from the group consisting of sodium oleate, potassium oleate, sodium stearate, sodium deoxycholate and mixtures of two or more thereof, more preferably the at least on anionic surfactant is sodium oleate, potassium oleate or a mixture thereof. Most preferably, the composition comprises sodium oleate as the at least one anionic surfactant.

The total amount of anionic surfactants within the composition, is preferably in the range of from 0.01 to 5% by weight, more preferably 0.05 to 1% by weight, more preferably in the range of from 0.01% by weight to 0.5% by weight, such as 0.01, 0.02, 0.03, 0.04, 0.05, 0.06, 0.07, 0.08, 0.09, 0.1, 0.2, 0.3, 0.4 or 0.5% by weight, based on the total weight of the composition.

Preferably the composition comprises sodium oleate in an amount in the range of from 0.01 to 5% by weight, more preferably 0.05 to 1% by weight, more preferably in the range of from 0.01% by weight to 0.5% by weight, such as 0.01, 0.02, 0.03, 0.04, 0.05, 0.06, 0.07, 0.08, 0.09, 0.1, 0.2, 0.3, 0.4 or 0.5% by weight, based on the total weight of the composition.

The Amphoteric Surfactant

The term "amphoteric surfactant" refers to surfactants which carry a charge that varies depending on the pH of the solution. At low pH (acidic conditions), they act as cationic surfactants while at high pH (basic), they act as anionic surfactants. When both charge groups are permanent, the surfactants are sometimes also called zwitterionic.

Preferably, the at least one amphoteric surfactant is lecithin. Within the meaning of the present invention the term "lecithin" refers to a naturally occurring or synthetic lecithin that which may be suitably refined. Suitable lecithins include, but are not limited to, lecithins derived from egg, corn or soybean or mixtures thereof. Further suitable lecithins include, but are not limited to, dihexanoyl-L-alpha-lecithin, dioctanoyl-L-alpha-lecithin, didecanoyl-L-alpha-lecithin, didodecanoyl-L-alpha-lecithin, ditetradecanoyl-L-alpha-lecithin, dihexadecanoyl-L-alpha-lecithin, dioctadecanoyl-L-alpha-lecithin, dioleoyl-L-alpha-lecithin, dilinolenoyl-L-alpha-lecithin and alpha-palmitol. Lecithins are typically mixtures of diglycerides of fatty acids linked to the choline ester of phosphoric acid and can contain differing amounts of other compounds depending on the method of isolation. Typically, commercial lecithin is a mixture of acetone-insoluble phosphatides. Preferably, the lecithin is obtained from egg or from seeds including soybean and corn, using methods well known in the art. Lecithin obtained from soybean is referred to herein as soy lecithin. Lecithin obtained from egg is referred to herein as egg lecithin.

Preferably, the composition comprises lecithin as amphoteric surfactant, more preferably lecithin selected from the group consisting of an egg lecithin, a soy lecithin, and a mixture thereof.

As to the soy lecithin, said soy lecithin typically comprises at least 50% by weight of phospholipids, more preferably of from 50 to 95% by weight, more preferably of from 70 to 80% by weight and most preferably of from 75 to 85% by weight, based on the total weight of the soy lecithin. The soy lecithin, as described above, usually comprises at least phosphatidylcholine and phosphatidylethanolethanolamine, and usually further comprises phosphatidylinositol and phosphatidic acid. A typical composition comprises phosphatidylcholine in an amount in the range of from 70% by weight to 80% by weight and phosphatidylethanolethanolamine in an amount in the range of from 5 to 10% by weight, based on the total weight of the soy lecithin. Such soy lecithin is commercially available, for example as Epikurin™170.

As to the egg lecithin, said egg lecithin typically comprises at least 50% by weight of phospholipids, preferably at least 80% by weight, more preferably at least 90% by weight, based on the total weight of the egg lecithin.

The egg lecithin, as described above, usually also comprises phosphatidylcholine, phosphatidylethanolethanolamine, phosphatidylinositol and phosphatidic acid. A typical composition comprises phosphatidylcholine in an amount in the range of from 60 to 85% by weight and phosphatidylethanolethanolamine in an amount in the range of from 7 to 18% by weight, based on the total weight of the egg lecithin. Such egg lecithins are commercially available, for example as PL 90 or Lipoid E80.

It is to be understood that lecithin may be employed in combination with other amphoteric surfactants. Preferably, the composition only comprises lecithin as amphoteric surfactant.

Thus, the present invention also relates to a composition for parenteral administration comprising an aqueous phase and 5 to 30% by weight of an oil phase based on the total weight of the composition, wherein the oil phase comprises omega-3 fatty acid ethylester selected from the group consisting of eicosapentaenoic acid ethylester, docosahexaenoic acid ethylester and mixtures thereof, and wherein the composition further comprises at least one anionic surfactant and at least one amphoteric surfactant, and wherein the composition comprises less than 0.05% by weight of oleic acid, based on the total weight of the composition, and wherein the at least one amphoteric surfactant is lecithin.

Further, the present invention relates to a method for preparing a composition as described above as well as to a composition obtained or obtainable by the above described method, the composition comprising an aqueous phase and 5 to 30% by weight of an oil phase based on the total weight of the composition, wherein the oil phase comprises omega-3 fatty acid ethylester selected from the group consisting of eicosapentaenoic acid ethylester, docosahexaenoic acid ethylester and mixtures thereof, and wherein the composition further comprises at least one anionic surfactant and at least one amphoteric surfactant, and wherein the composition comprises less than 0.05% by weight of oleic acid, based on the total weight of the composition, and wherein the at least one amphoteric surfactant is lecithin.

The total amount of amphoteric surfactants within the composition, more preferably of lecithin, is preferably in the range of from 0.5 to 5% by weight, more preferably 0.75 to 3% by weight, more preferably in the range of from 1% by weight to 2% by weight, such as 1.0, 1.1, 1.2, 1.3, 1.4, 1.5, 1.6, 1.7, 1.8, 1.9 or 2.0% by weight, based on the total weight of the composition.

Other Surfactants

It is noted that the composition as described above may comprise any other suitable surfactant. As suitable other surfactants, non-ionic surfactants may be mentioned. Thus, also in the method described above, any other suitable surfactant may be added, such as in particular in step (a).

The term non-ionic surfactant refers to compounds which do not ionize in aqueous solutions, i.e. their hydrophilic group(s) does/do not dissociate in aqueous solution. Examples include alcohols, phenols, ethers, esters and amides. As examples polyoxyl 35 castor oil (Cremophor® EL), polyoxyethyleneglycol-660-hydroxystearate (Solutol® H15), polyoxyethylene sorbitan monolaurates (Tween® 10, 40 or 80), sorbitan monolaurate (Span® 20), polyoxyethylene-polyoxypropylene block copolymers (Poloxamer 188) may be mentioned.

Preferably the composition comprises less than 1% by weight, more preferably less than 0.9% by weight, more preferably less than 0.8% by weigh, more preferably less than 0.7% by weight, more preferably less than 0.6% by weight, more preferably less than 0.5% by weight, more preferably less than 0.4% by weight, more preferably less than 0.3% by weight, more preferably less than 0.2% by weight, more preferably less than 0.1% by weight, more preferably less than 0.05% by weight, more preferably less than 0.03% by weight, more preferably less than 0.02% by weight, more preferably essentially no, more preferably no, non-ionic surfactant, calculated as the sum of all non-ionic surfactants and based on the total weight of the composition. Again, the term "essentially no" in this context refers to embodiments wherein essentially no, that is an amount of <0.01% by weight including 0% by weight, non-ionic surfactants are present in or added to the composition.

Co-Surfactant

A co-surfactant is an amphiphilic molecule, i.e. a molecule that contains both hydrophilic and lipophilic groups. Usually a co-surfactant substantially accumulates with the surfactant at the interfacial layer. The hydrophile-lipophile balance (HLB) number is used as a measure of the ratio of hydrophilic and lipophilic groups present in a surfactant or co-surfactant, respectively. Usually a co-surfactant with a very low HLB value (thus with a relatively high affinity to oil) is used together with a surfactant with a high HLB to modify the overall HLB of the system. Unlike the surfactant, the co-surfactant may not be capable of forming self-associated structures, like micelles, on its own. Several kinds of molecules including nonionic surfactants, alcohols, amines and acids, can function as co-surfactants in a given system. The quantity of a co-surfactant in a system is usually less than that of the surfactant and it often serves to modify the overall HLB value of the system. The co-surfactant has the effect of further reducing the interfacial tension, whilst increasing the fluidity of the interface. Co-surfactants may also adjust the curvature of the interfacial film by partitioning between the tails of the surfactant chains, allowing greater penetration of the oil between the surfactant tails.

The composition may additionally comprise at least one co-surfactant, provided that the composition comprises less than 0.05% by weight of oleic acid.

Surprisingly it has been found that compositions comprising less than 0.05% by weight of oleic acid are advantageous with respect to their stability.

Preferably the composition comprises less than 0.05% by weight, more preferably less than 0.04% by weight, more preferably less than 0.03% by weight, more preferably less than 0.02% by weight, more preferably essentially no, more preferably no oleic acid. Thus, also in the method described above, preferably, less than 0.05% by weight of oleic acid, more preferably less than 0.04% by weight of oleic acid, more preferably less than 0.03% by weight of oleic acid, more preferably less than 0.02% by weight of oleic acid, more preferably essentially no, more preferably no (0% by weight) oleic acid is added during the method. The term "essentially no" in this context refers to embodiments wherein essentially no, that is an amount of <0.01% by weight including 0% by weight is present or added.

Co-Solvent

The composition may comprise at least one co-solvent. The term co-solvent refers to molecules that may increase the stability of the composition according to the invention. In addition to making the environment more hydrophobic by reducing the dielectric constant of water, co-solvents increase the amount of molecularly dispersed surfactant in the aqueous phase. Availability of free surfactant aids in the solubilisation of hydrophobic molecules by creating pockets of hydrophobic regions within the aqueous phase.

Examples of co-solvents include ethanol, propylene glycol and polyethylene glycol (PEG).

Preferably, the composition comprises less than 1% by weight, more preferably less than 0.9% by weight, more preferably less than 0.8% by weigh, more preferably less than 0.7% by weight, more preferably less than 0.6% by weight, more preferably less than 0.5% by weight, more preferably less than 0.4% by weight, more preferably less than 0.3% by weight, more preferably less than 0.2% by weight, more preferably less than 0.1% by weight, more preferably less than 0.05% by weight, more preferably less than 0.03% by weight, more preferably less than 0.02% by weight, more preferably essentially no, more preferably no, polyethylene glycol and propylene glycol, calculated as the sum of both components and based on the total weight of the composition.

The term "essentially no" in this context refers to embodiments wherein essentially no, that is an amount of <0.01% by weight including 0% by weight, of the components, that is of polyethylene glycol and propylene glycol, are present in or added to the composition.

Thus, the present invention also relates to a composition for parenteral administration as described above, as well as to a composition obtained or obtainable by the above described method, wherein the composition comprises less than 1% by weight, more preferably less than 0.9% by weight, more preferably less than 0.8% by weigh, more preferably less than 0.7% by weight, more preferably less than 0.6% by weight, more preferably less than 0.5% by weight, more preferably less than 0.4% by weight, more preferably less than 0.3% by weight, more preferably less than 0.2% by weight, more preferably less than 0.1% by weight, more preferably less than 0.05% by weight, more preferably less than 0.03% by weight, more preferably less than 0.02% by weight, more preferably essentially no, more preferably no, polyethylene glycol and propylene glycol, calculated as the sum of both components and based on the total weight of the composition.

Further, the present invention relates to a method for preparing such a composition as well as to such a composition obtained or obtainable by said method, wherein less than 1% by weight, more preferably less than 0.9% by weight, more preferably less than 0.8% by weigh, more preferably less than 0.7% by weight, more preferably less than 0.6% by weight, more preferably less than 0.5% by weight, more preferably less than 0.4% by weight, more preferably less than 0.3% by weight, more preferably less than 0.2% by weight, more preferably less than 0.1% by weight, more preferably less than 0.05% by weight, more preferably less than 0.03% by weight, more preferably less than 0.02% by weight, of polyethylene glycol and propylene glycol, more preferably essentially no, more preferably no, polyethylene glycol and propylene glycol, calculated as the sum of both components and based on the total weight of the composition, are added during the method.

Thus, the composition for parenteral administration comprises less than 1% by weight, more preferably less than 0.9% by weight, more preferably less than 0.8% by weigh, more preferably less than 0.7% by weight, more preferably less than 0.6% by weight, more preferably less than 0.5% by weight, more preferably less than 0.4% by weight, more preferably less than 0.3% by weight, more preferably less than 0.2% by weight, more preferably less than 0.1% by weight, more preferably less than 0.05% by weight, more preferably less than 0.03% by weight, more preferably less than 0.02% by weight, more preferably essentially no, more preferably no, co-solvents, calculated as the sum of all co-solvents, and based on the total weight of the composition, wherein the co-solvents.

Surprisingly it has been found that compositions comprising less than 1% by weight of polyethylene glycol and propylene glycol, calculated as the sum of both components and based on the total weight of the composition are advantageous with respect to their stability.

Tonicity Agent

Tonicity agents are substances which are used to confer tonicity to e.g. pharmaceutical compositions.

Preferably, the composition according to the invention comprises at least one tonicity agent.

A tonicity agent useful in the present composition can be any pharmaceutically acceptable tonicity agent. Common tonicity agents include, but are not limited to, agents selected from the group consisting of sodium chloride, mannitol, lactose, dextrose (hydrous or anhydrous), sucrose, glycerol, and sorbitol, and solutions of the foregoing.

Thus, according to a preferred embodiment of the invention, the present invention also relates to a composition, as described above, as well as to a composition obtained or obtainable by the above described method, wherein the composition comprises at least one tonicity agent.

Preferably, the tonicity agent is glycerol.

If present, preferably the total amount of tonicity agents present is in the range of 0 to 10% by weight, more preferably from 1 to 5% by weight, more preferably from 1 to 4% by weight, more preferably from 1 to 3% by weight, more preferably from 1.5 to 2.8% by weight, and even more preferably from 2.0 to 2.5% by weight, based on the total weight of the composition.

Preferably, the composition has an osmolality in the range 305 to 420 mOsmol/kg, more preferably in the range of from 300 to 420 mOsmol/kg, measured with a Vapor Pressure Osmometer, Model 5520 (Vapro™) according to USP <785>.

Antioxidant

Preferably, the composition according to the invention comprises at least one agent with antioxidant activity, preferably at least two agents with antioxidant activity.

An antioxidant useful in the present composition can be any pharmaceutically acceptable compound having antioxidant activity including sodium metabisulfite, sodium bisulfite, sodium sulfite, sodium thiosulfate, sodium formaldehyde sulfoxylate, sodium formaldehyde bisulfite, thioglycerol, thiosorbitol, thioglycolic acid, cysteine hydrochloride, n-acetyl-cysteine, citric acid, alpha-tocopherol, beta-tocopherol, gamma-tocopherol, Trolox (soluble form of vitamin E), butylated hydroxyanisole (BHA), butylated hydroxytoluene (BHT), t-butylhydroquinone (TBHQ), monothioglycerol, propyl gallate, lopurinol, carnosine, histidine, enzymes, such as superoxide dismutase, catalase, selenium glutathione peroxidase, phospholipid hydroperoxide and glutathione peroxidase, Coenzyme Q 10, tocotrienols, carotenoids, quinones, bioflavonoids, polyphenols, bilirubin, ascorbic acid, isoascorbic acid, uric acid, metal-binding proteins, ascorbic acid palmitate, an antioxidant obtained or obtainable from rosemary and rosemary extract.

The at least one agent with antioxidant activity is in particular selected from the group consisting of alpha-tocopherol, beta-tocopherol, gamma-tocopherol, ascorbic acid, and mixtures of two or more thereof.

If present, the total amount of agents with antioxidant activity is preferably in the range of from 0.01 to 0.05% by weight, more preferably from 0.01 to 0.04% by weight, more preferably from 0.01 to 0.03% by weight, and even more preferably from 0.015 to 0.025 by weight, based on the total weight of the composition.

Thus, the present invention also relates to a composition as described above as well as to a composition obtained or obtainable by the above described method, wherein the composition comprises at least one agent with antioxidant activity. Preferably, the composition further comprises at least one tonicity agent.

More preferably, the composition comprises at least two agents with antioxidant activity which differ from each other. For example, the present invention comprises alpha-tocopherol and beta-tocopherol, or alpha-tocopherol and gamma-tocopherol, or beta-tocopherol and gamma-tocopherol, or alpha-tocopherol and ascorbic acid, or beta-tocopherol and ascorbic acid, or gamma-tocopherol and ascorbic acid.

According to a further preferred embodiment, the present invention comprises a mixture of beta-tocopherol, alpha-tocopherol and gamma-tocopherol.

Further Additives

It is to be understood that other physiologically safe additives may also be present in the composition according to the invention including, but not limited to, common intravenous salts such as sodium chloride and nonelectrolytes such as glucose, pH modifiers (such as acetic acid and sodium acetate) and buffers (such as acetate, lactate, and phosphate buffer systems composed of the acid and a salt of the acid) as well as selenium compounds.

One skilled in the art will understand that the pH of the composition may for example be adjusted through the use of buffers, such as phosphate buffers, or neutralization agents, such as sodium hydroxide.

Preferably, the composition according to the present invention has a pH value close to physiological pH or above since it is contemplated that at such pH values the fatty acids are less prone to peroxidation.

The final pH of the composition is preferably in the range of from 7.0 to 10, preferably in the range of from 8 to 10, more preferably in the range of from 8 to 9.

By way of example, the composition may further comprise other additives conventionally used in pharmaceutical compositions. Such additives include carbohydrate nutrients, electrolytes, amino acids, vitamins, trace minerals, preservatives, anti-foaming agents, buffering agents, chelating agents, and mixtures thereof. The amounts of such additives can be readily determined by one skilled in the art according to the particular properties desired.

The Method for Preparing the Composition

As described above, the present invention also relates to a method for preparing a composition for parenteral administration and to a composition obtained or obtainable by said method the composition comprising an aqueous phase and 5 to 30% by weight of an oil phase, based on the total weight of the composition, wherein the oil phase comprises omega-3 fatty acid ethylester selected from the group consisting of eicosapentaenoic acid ethylester, docosahexaenoic acid ethylester and mixtures thereof, and wherein the composition further comprises at least one anionic surfactant and at least one amphoteric surfactant, and wherein the composition comprises less than 0.05% by weight of oleic acid, based on the total weight of the composition, wherein the method comprises:

(a) providing an aqueous phase comprising the at least one amphoteric surfactant and the at least one anionic surfactant, (b) providing an oil phase comprising omega-3 fatty acid ethylester selected from the group consisting of eicosapentaenoic acid ethylester, docosahexaenoic acid ethylester and mixtures thereof, (c) mixing the oil phase according to (b) with the aqueous phase according to (a).

It is to be understood that any one of the optional further components of the composition may be added in any one of steps (a) to (c), or in one or more additional steps.

Step (a)

Step (a) is preferably carried out by dispersing the at least one anionic surfactant and the at least one amphoteric surfactant together or subsequently in water or in an aqueous solution. The dispersion step is preferably carried out at a temperature in the range of from 25 to 70° C., wherein during this step, the temperature may be varied or held essentially constant.

Preferably, initially, the at least one anionic surfactant is dispersed in water and the resulting mixture is mixed for example with a high shear mixer. Preferably, the mixture is then heated to a temperature in the range of from 40 to 70° C., preferably, 50 to 65° C., more preferably 55 to 60° C., preferably for a time in the range of from 1 min to 2 h, more preferably of from 10 min to 15 min.

Preferably, subsequently, the at least one amphoteric surfactant is added to the mixture comprising water and the at least one anionic surfactant. The resulting mixture is again mixed for example with a high shear mixer. Preferably, the mixing is carried out at a temperature in the range of from 25 to 70° C., preferably for a time in the range of from 1 min to 2 h, more preferably of from 10 to 15 min.

It is to be understood that in step (a) further additives, such as at least one co-surfactant and/or at least one co-solvent, may be added.

For example, in case the composition comprises at least one tonicity agent, this may be in principle added in any step of the method described above. According to one preferred embodiment, this additive, if present, is added in step (a). Thus, preferably step (a) further comprises adding at least one tonicity agent to the aqueous phase or mixing the tonicity agent with water to give an aqueous solution, more preferably wherein the tonicity agent is glycerol. These additives may thus be added prior to or after the addition of the at least one anionic surfactant and/or the at least one amphoteric surfactant.

Preferably, step (a) further comprises adjusting the pH of the aqueous phase, such as through the use of buffers, such as phosphate buffers, or neutralization agents, such as sodium hydroxide, to a desired pH which is preferably in the range of from 7.0 to 10, more preferably in the range of from 8 to 10, and more preferably in the range of from 8 to 9.

Step (b)

As outlined above, initially a mixture comprising EPA and DHA ethylester is provided, wherein the EPA and DHA ethylester may be obtained by any way known to those skilled in the art. This mixture may preferably already comprise further components such as the at least one agent with antioxidant activity. Alternatively, these agents may be added in step (a) and/or (b), preferably in b), or in any other step of the method, described above.

Preferably, the oil phase is heated in step (b), that is prior to step (c), to a temperature in the range of from 30 to 70° C., more preferably from 40 to 65° C., more preferably from 50 to 60° C., more preferably to a temperature around 55° C., preferably for a time in the range of from 1 min to 30 min, more preferably from 3 min to 20 min, more preferably from 5 min to 15 min.

The oil phase is preferably homogenized, preferably at a temperature in range of from 30 to 70° C., more preferably from 40 to 65° C., more preferably from 50 to 60° C., more preferably to a temperature around 55° C.

According to one embodiment, the at least one agent with antioxidant activity, if present, is additionally added in step (b). Thus, in this case, in step (b) optionally at least one agent with antioxidant activity is added to the mixture of EPA ethylester and/or DHA ethylester, more preferably at least one tocopherol is added in step (b). According to an alternative embodiment, the at least one tocopherol is already present in the mixture provided in step (b), i.e. the mixture comprising EPA ethylester and DHA ethylester.

Thus, step (b) preferably comprises providing an oil phase by mixing EPA ethylester and/or DHA ethylester with the at least one agent with antioxidant activity or providing an oil phase comprising EPA ethylester and/or DHA ethylester and the at least one agent with antioxidant activity, wherein at least 60% by weight of the oil phase consist of EPA ethylester and/or DHA ethylester.

It is to be understood that in step (b) further additives may be added.

Step (c)

The method further comprises mixing the oil phase according to (b) with the aqueous phase according to (a) to give a mixture of oil phase and an aqueous phase. Preferably, thereby a pre-emulsion or an emulsion is formed. The mixing may be carried out by any methods known to those skilled in the art. Preferably, the mixing is carried out using a high shear mixer.

Preferably, the oil phase is added to the aqueous phase or vice versa at a temperature in the range of from 50 to 70° C., more preferably from 55 to 65° C.

Preferably the oil phase is added to the aqueous phase or vice versa at a pressure, such as under nitrogen pressure, in the range of from 0.20 to 0.80 bar, more preferably from 0.20 to 0.40 bar, such as at around 0.30 bar. During this step, pressure may be varied or held essentially constant.

According to a preferred embodiment, the mixture is stirred for a time in the range of from 1 min to 1 h, preferably of from 10 min to 30 min, to give a pre-emulsion. During this step, the temperature may be varied or held essentially constant.

It is to be understood that further components may also be added after the formation of the pre-emulsion.

According to a preferred embodiment, the pH of the pre-emulsion is adjusted to a pH in the range of from 8 to 10, in particular by adding sodium hydroxide, if necessary.

Step (d)

Preferably, the method further comprises the homogenization of the mixture obtained from step (c). This homogenization may be carried out by any suitable methods known to those skilled in the art.

Preferably, the mixture is homogenized at temperature in range of from 40 to 70° C., more preferably from 50 to 70° C., more preferably from 50 to 60° C.

Preferably, the mixture is homogenized at a pressure in the range of from 400 to 600 bar, more preferably from 450 to 550 bar. During this step, the pressure may be varied or held essentially constant.

Preferably, the homogenization may for example be carried out using a high pressure homogenizer or a microfluidizer.

Thus, the present invention also relates to a method as described above for preparing a composition for parenteral administration, as well as to a composition obtained or obtainable by said method, the method further comprising:

(d) homogenizing the mixture, preferably the pre-emulsion, obtained in step (c) at a temperature in the range of from 50 to 60° C. and preferably at a pressure in the range of from 450 to 550 bar.

After the homogenization step, further steps may be carried out, such as purification steps or filtration steps.

Step (e)

Preferably, the composition obtained in (c) or (d) is sterilized to ensure its suitability for parenteral administration.

The sterilization may be carried out by any suitable methods known to those skilled in the art. In particular, the sterilization is carried out by autoclaving, preferably at a temperature in the range of from 119° C. to 122° C., more preferably at a temperature of around 121° C., preferably for a time in the range of from 1 min to 30 min preferably of from 10 min to 15 min.

Thus, the present invention also relates to a method as described above for preparing a composition for parenteral administration as well as to a composition obtained or obtainable by said method, the method further comprising (e) autoclaving the mixture obtained from (c) or (d), preferably from (d), at a temperature in the range of from 119° C. to 122° C. for a time in the range of from 10 min to 15 min.

It is to be understood that the preparation of the composition preferably takes place under GMP standardized conditions in order to ensure quality, safety and effectiveness of the composition when used as a medicament or in parenteral nutrition. Further criteria for an ingredient or a composition being pharmaceutically acceptable can be derived from approval regulations by a regulatory agency and/or generally recognized pharmacopoeias.

As described above, the present invention also relates to a composition for parenteral administration as described above, or a composition for parenteral administration obtained or obtainable by the above described method, for use as a medicament. Further, the present invention relates to a medicament comprising the composition for parenteral administration as described above, or a composition for parenteral administration obtained or obtainable by the above described method. Further, the present invention relates to a composition for parenteral administration as described above, or a composition for parenteral administration obtained or obtainable by the above described method, for use in providing nutrition to a patient in need thereof.

The term "parenteral administration" as used herein means that the administration is not through the gastrointestinal tract, but rather through some other route, such as via the subcutaneous, intramuscular, intravenous, intradermal or intraspinal route. "Intravenous" is understood to mean administration into a venous blood vessel.

Preferably, the composition as described above, or the composition obtained or obtainable by the above described method, is administered intravenously. "Intravenous" is understood to mean administration into a venous blood vessel.

The composition may be injected or administered via infusion. Injection refers to administration using a syringe. Generally, a bolus is administered. However, injection or infusion by means of syringe-pumps is also possible. The term "infusion" refers to the continuous administration of the composition into a blood vessel which, for example, can be effected via a peripheral or central venous catheter.

Preferably, the composition as described above, or the composition obtained or obtainable by the above described method, is administered via infusion. Thus, according to a preferred embodiment, the present invention also relates to an infusion bag comprising the composition as described above, or the composition obtained or obtainable by the above described method.

It is to be understood that the preparation of the composition preferably takes place under GMP standardized conditions in order to ensure quality, pharmaceutical regulations safety and effectiveness of the composition when used as a medicament or in parenteral nutrition. Further criteria for an ingredient or a composition being pharmaceutically acceptable can be derived from approval regulations by a regulatory agency and/or generally recognized pharmacopoeias.

As described above, the present invention also relates to a composition as described above, or a composition for parenteral administration obtained or obtainable by the above described method, for use as a medicament. Preferably, the said composition is administered parenterally.

Further the present invention relates to a medicament comprising the composition for parenteral administration as described above, or a composition for parenteral administration obtained or obtainable by the above described method. Further, the present invention relates to a composition for parenteral administration as described above, or a composition for parenteral administration obtained or obtainable by the above described method, for use in providing nutrition to a patient in need thereof.

The term "parenterally" as used herein refers to a mode of administration. Preferably, the term includes subcutaneous, intramuscular, intravenous, intradermal or intraspinal administration. Preferably, the term does not encompass administration through the gastrointestinal tract, in particular through oral administration.

It is to be understood that the composition of the present invention is administered in an effective amount, in particular in a therapeutically effective amount, i.e. in an amount which allows for the treatment of a disease as referred to herein below. Whether an amount of the composition is effective or not can be determined by the skilled person without further ado.

Preferably, the present invention also relates to a composition for parenteral administration as described above, or a composition for parenteral administration obtained or obtainable by the above described method, for use in treating stroke, sepsis, Alzheimer's disease or cancer. Further, the present invention also relates to a composition for parenteral administration as described above, or a composition for parenteral administration obtained or obtainable by the above described method, for use in providing nutrition to a patient suffering from at least one disease selected from stroke, sepsis, Alzheimer's disease or cancer.

Likewise, the present invention also relates to a method for treating stroke, sepsis, Alzheimer's disease or cancer comprising parenterally administering the composition as described above, or the composition obtained or obtainable by the above described method, to a patient in need thereof. Further, the present invention relates to a method of providing parenteral nutrition to a patient suffering from at least one disease selected from stroke, sepsis, Alzheimer's disease or cancer, the method comprising administering a composition as described above, or a composition obtained or obtainable by the above described method, preferably parenterally, more preferably intravenously, to the patient.

The term "treatment" or "treating" as used herein in the context of treating a disease pertains generally to treatment and therapy of a patient in which some desired therapeutic effect is achieved, for example the inhibition of the progress of a symptom associated with a disease, such as stroke, sepsis, Alzheimer's disease or cancer, and includes a reduction in the rate of progress, a halt in the rate of progress, amelioration of the symptom, and cure of the symptom. Treatment as a prophylactic measure (i.e. prophylaxis) is also included.

Preferably, the composition according to the present invention is used for the treatment and/or for the parenteral nutrition of a human patient. Preferably, the patient shall suffer from at least one disease selected from the group consisting of stroke, sepsis, Alzheimer's disease and cancer.

According to a preferred embodiment, the present invention relates to a composition for parenteral administration as described above, or a composition for parenteral administration obtained or obtainable by the above described method, for use in treating stroke.

Stroke is the rapidly developing loss of brain function(s) due to disturbance in the blood supply to the brain. This can be due to ischemia (lack of blood flow) caused by blockage (thrombosis, arterial embolism), or a hemorrhage (leakage of blood). The etiology of stroke is either ischemic, as in the majority of cases, or hemorrhagic. Ischemic stroke is usually caused by an embolus or a thrombus. The methods of the invention encompass treatment of either ischemic or hemorrhagic stroke via intravenous administration of the compositions described herein. After a massive cell death in the immediate core of the infarct caused by glucose and oxygen deficiency (cerebral ischemia), the zone of infarction grows for a few days due to secondary mechanisms such as glutamate excitotoxicity, inflammatory mechanisms, the production of free radicals and apoptotic mechanisms. The methods of the invention encompass prevention and/or reduction of these secondary mechanisms to reduce the zone of infarction by intravenous administration of the compositions described herein. According to a further embodiment, the present invention relates to a composition for parenteral administration as described above, or a composition for parenteral administration obtained or obtainable by the above described method, for use in providing nutrition to a patient suffering from stroke. Further, the present invention relates to a method of providing parenteral nutrition to a patient suffering from stroke.

According to a further embodiment, the present invention relates to a composition for parenteral administration as described above, or a composition for parenteral administration obtained or obtainable by the above described method, for use in treating cancer. For example, it has been suggested that omega-3 fatty acids can improve the response to chemotherapy of various cancers by enhancing cytotoxicity of anti-cancer drugs and by reducing oxidative stress. Thus, it is contemplated that the compositions of the present invention can improve the clinical outcomes by accentuating the response to primary cytotoxic drugs in cancer therapy. Further, the present invention relates to a composition for parenteral administration as described above, or a composition for parenteral administration obtained or obtainable by the above described method, for use in providing nutrition to a patient suffering from cancer. Further, the present invention relates to a method of providing parenteral nutrition to a patient suffering cancer.

According to a further embodiment, the present invention relates to a composition for parenteral administration as described above, or a composition for parenteral administration obtained or obtainable by the above described method, for use in treating sepsis, in particular for treatment for endotoxicosis during severe sepsis, or for use in providing nutrition to a patient suffering from sepsis. Further, the present invention relates to a method of providing parenteral nutrition to a patient suffering from sepsis.

The term "sepsis" as used herein refers to a medical condition which is caused by the response of the immune system to an infection. This response is called systemic inflammatory response syndrome (SIRS). Sepsis can proceed to severe sepsis, septic shock, refractory septic shock or multi-organ dysfunction syndrome (MODS). The latter conditions are associated with organ dysfunction, e.g. the cardiovascular, the renal, the respiratory, the cerebral or the hematologic system.

According to a further embodiment, the present invention relates to a composition for parenteral administration as described above, or a composition for parenteral administration obtained or obtainable by the above described method, for use in treating Alzheimer's disease or for use in providing nutrition to a patient suffering from Alzheimer's disease. Further, the present invention relates to a method of providing parenteral nutrition to a patient suffering from Alzheimer's disease.

The term "Alzheimer's disease" is well known in the art. As used herein, the term refers to a progressive mental deterioration which is manifested by memory loss, confusion and disorientation. The disease is usually beginning in late middle life and results in death within five to ten years. Alzheimer's disease can be diagnosed by methods well known in the art. It is characterized by thickening, conglutination, and distortion of the intracellular neurofibrils, neurofibrillary tangles and senile plaques composed of granular or filamentous argentophilic masses with an amyloid core.

In the following, especially preferred embodiments of the present invention are described by way of example:

1. A composition for parenteral administration comprising an aqueous phase and 5 to 30% by weight of an oil phase, based on the total weight of the composition, wherein the oil phase comprises omega-3 fatty acid ethylesters selected from the group consisting of eicosapentaenoic acid ethylester, docosahexaenoic acid ethylester and mixtures thereof, and wherein the composition further comprises at least one anionic surfactant and at least one amphoteric surfactant, and wherein the composition comprises less than 0.05% by weight of oleic acid, based on the total weight of the composition.
2. The composition according to embodiment 1, wherein at least 60% by weight of the oil phase consist of omega-3 fatty acid ethylester selected from the group consisting of eicosapentaenoic acid ethylester, docosahexaenoic acid ethylester and mixtures thereof.
3. The composition according to embodiment 1, wherein the oily phase comprises a mixture of eicosapentaenoic acid ethylester and docosahexaenoic acid ethylester and wherein the weight ratio of eicosapentaenoic acid ethylester:docosahexaenoic acid ethylester is in the range of from 1:9 to 9:1.
4. The composition according any one of embodiments 1 to 3, wherein the oil phase comprises less than 1% by weight medium chain triglycerides, based on the total weight of the composition.
5. The composition according to any one of embodiments 1 to 4, being an oil-in-water emulsion having a mean droplet particle size in the range 0.1-0.3 μm, measured with an LS 13 320 Laser Diffraction Particle Size Analyser (Beckman Coulter), according to USP <729>.
6. The composition according to any one of embodiments 1 to 5, comprising at least one agent with antioxidant activity, preferably at least two agents with antioxidant activity.
7. The composition according to embodiment 6, wherein the at least one agent with antioxidant activity is selected from the group consisting of alpha-tocopherol, beta-tocopherol, gamma-tocopherol, ascorbic acid, ascorbic acid palmitate, an antioxidant obtained or obtainable from rosemary, rosemary extract and mixtures of two or more thereof.
8. The composition according to embodiment 6 or 7, wherein the total amount of agents with antioxidant activity is in the range of from 0.01 to 0.05% by weight, based on the total weight of the composition.
9. The composition according to any one of embodiments 1 to 8, wherein the at least one amphoteric surfactant is lecithin.
10. The composition according embodiment 9, wherein the lecithin is selected from the group consisting of an egg lecithin, a soy lecithin, and a mixture thereof.
11. The composition according to embodiment 9 or 10, wherein the total amount of lecithin is in the range of from 1 to 2% by weight, based on the total weight of the composition.
12. The composition according any one of embodiments 1 to 11, wherein the at least one anionic surfactant is sodium oleate.
13. The composition according to any one of embodiments 1 to 12, wherein the total amount of the at least one anionic surfactant is in the range of from 0.01 to 0.5% by weight, based on the total weight of the composition.
14. The composition according to any one of embodiments 1 to 13 wherein the composition comprises at least one tonicity agent.
15. The composition according embodiment 14, wherein the tonicity agent is glycerol.
16. The composition according to embodiment 14 or 15, wherein the total amount of the at least one tonicity agent is in the range of from 1 to 3% by weight, based on the total weight of the composition.
17. The composition according to any one of embodiments 14 to 16, wherein the composition has an osmolality in the range 305-420 mOsmol/kg, measured with a Vapor Pressure Osmometer, Model 5520 (Vapro™) according to USP <785>.

18. The composition according to any one of embodiments 1 to 17, wherein the composition comprises in sum less than 1% by weight, preferably less than 0.1% by weight, preferably less than 0.01% by weight, of polyethylene glycol and propylene glycol, based on the total weight of the composition.
19. The composition according to any one of embodiments 1 to 17, wherein the composition comprises less than 1% by weight, preferably less than 0.1% by weight, co-solvents, calculated as the sum of all co-solvents, and based on the total weight of the composition.
20. The composition according to any one of embodiments 1 to 19, wherein the composition comprises less than 0.01% by weight, more preferably essentially no oleic acid.
21. A method for preparing a composition for parenteral administration comprising an aqueous phase and 5 to 30% by weight of an oil phase, based on the total weight of the composition, wherein the oil phase comprises omega-3 fatty acid ethylester selected from the group consisting of eicosapentaenoic acid ethylester, docosahexaenoic acid ethylester and mixtures thereof, and wherein the composition further comprises at least one anionic surfactant and at least one amphoteric surfactant, and wherein the composition comprises less than 0.05% by weight of oleic acid, based on the total weight of the composition, wherein the method comprises:
    a) providing an aqueous phase comprising the at least one amphoteric surfactant and the at least one anionic surfactant,
    b) providing an oil phase comprising omega-3 fatty acid ethylester selected from the group consisting of eicosapentaenoic acid ethylester, docosahexaenoic acid ethylester and mixtures thereof,
    c) mixing the oil phase according to (b) with the aqueous phase according to (a).
22. The method according to embodiment 21, wherein the oil phase is heated to 55° C. for a time in the range of from 5 min to 15 min prior to step (c).
23. The method according to embodiment 21 or 22, further comprising
    d) homogenizing the mixture obtained from (c) at a temperature in the range of from 50 to 60° C., preferably at a pressure in the range of from 450 to 550 bar.
24. The method according to any one of embodiments 21 to 23, further comprising
    e) autoclaving the mixture obtained from (c) or (d), preferably from (d), at a temperature in the range of from 119° C. to 122° C. for a time in the range of from 10 min to 15 min.
25. A composition obtained or obtainable by the method according to any one of embodiments 22 to 24.
26. A composition according to any one of embodiments 1 to 21 or 25 for use as a medicament.
27. A composition according to any one of embodiments 1 to 20 or 25 for use in treating stroke, sepsis, Alzheimer's disease or cancer.
28. A method for treating stroke, sepsis, Alzheimer's disease or cancer comprising intravenously administering the composition according to any one of embodiments 1 to 20 or 25 in a pharmaceutically effective amount to a patient in need thereof.
29. An infusion bag comprising the composition according to any one of embodiments 1 to 20 or 25.
30. The composition according to embodiment 26 or 27, wherein the composition is administered parenterally.
31. The composition according to embodiment 30, wherein the composition is administered intravenously.
32. A medicament comprising the composition according to any one of embodiments 1 to 20 or 25
33. A method of providing parenteral nutrition to a patient suffering from at least one disease selected from stroke, sepsis, Alzheimer's disease or cancer, the method comprising administering the composition according to any one of embodiments 1 to 20 or 25 to the patient.
34. The method of embodiment 33, wherein the composition is administered parenterally.
35. A composition according to any one of claim 1 to 20 or 25 for use in providing parenteral nutrition to a patient suffering from at least one disease selected from stroke, sepsis, Alzheimer's disease or cancer

Figure 1:
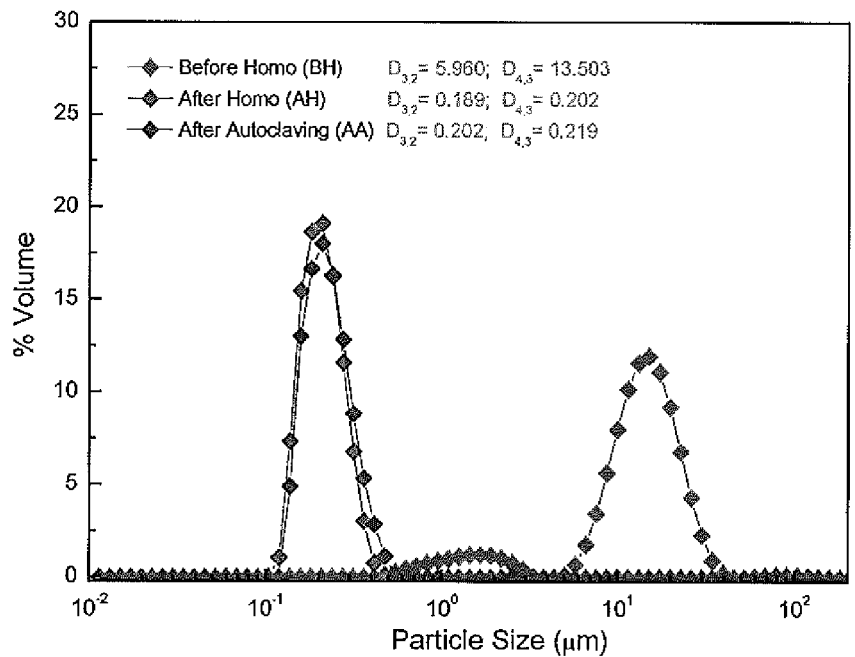
FIG. 1 shows the particle size distribution of composition 1 (as depicted in table 2, containing mixture 1) freshly prepared according to general procedure A containing 20% by weight of the oil phase measured with a LS 13 320 Laser Diffraction Particle Size Analyser (Beckman Coulter), according to USP <729>. The results comply with the requirements set forth in USP <729>.
Figure 2:
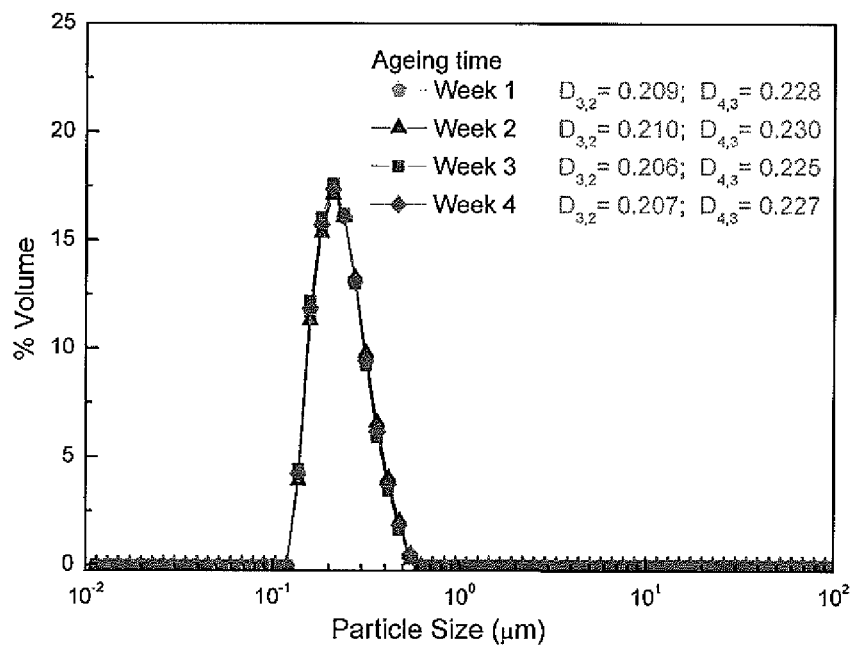
FIG. 2 shows the particle size distribution of the same composition as shown in FIG. 1, however after 1, 2, 3 and 4 weeks, measured with a LS 13 320 Laser Diffraction Particle Size Analyser (Beckman Coulter), according to USP <729>. The results comply with the requirements set forth in USP <729>.

The following examples are intended to illustrate the present invention without limiting it.

EXAMPLES

Different mixtures comprising highly concentrated omega-3 fatty acids (eicosapentaenoic acid (EPA) and docosahexaenoic acid (DHA)) as ethyl esters as obtained from Solutex S.L. were used.
Mixture 1:
    EPA ethylester (g/g) 0.6842
    DHA ethylester (g/g) 0.0838
Mixture 2:
    EPA ethylester (g/g) 0.1256
    DHA ethylester (gig) 0.6722
Mixture 3:
    EPA ethylester (g/g) 0.4501
    DHA ethylester (g/g) 0.2813

Example 1: General Procedure A for the Preparation of an Emulsion According to the Invention Using a shear mixer, first glycerol and sodium oleate, and then lecithin (PL90, obtainable from egg yolk (=egg lecithin with a phosphatidylcholine content of 64-79% and a phosphatidylethanolamine content of 10-18% by weight) were dispersed in water for injection, at a temperature between 55-60° C. The dispersion was continuously mixed until lecithin was homogeneously dispersed in water. Afterwards, the aqueous dispersion was submitted to ultrasonic treatment for 15 minutes. The PL90/sodium oleate/glycerol dispersion was then transferred to a separate container and an oily phase, containing highly-enriched omega-3 fatty acids with different EPA:DHA ratios (Mixtures 1 to 3), previously heated at 55° C., was added while continuously dispersing, using a Rayneri TURBOTEST high shear mixer, to obtain an oil-in-water emulsions with an oil phase concentration between 10 and 30% by weight. The coarse emulsion was then passed, six times through a homogenizer (Niro Soavi Panda Plus 2000), at 500 bar and temperature between 50-60° C. Finally, the emulsion was autoclaved at 122° C. for 15 min. A final lipid emulsion was obtained (see Table 1). The mean particle size of the lipid emulsions was measured using a Malvern Mastersizer 2000. The mixture was sterilized by autoclaving at a temperature of 120 to 122° C.

TABLE 1

General composition of the formulation prepared according to general example A

| | weight-% |
|---|---|
| Ingredients: | |
| Ethyl ester EPA/DHA | 20 |
| Egg lecithin | 1.2 |
| Sodium Oleate | 0.3 |
| Glycerol | 2.5 |
| Water for injection | adds up to 100 |
| Properties: | |
| pH after manufacture | 9-10 |
| Droplet size distribution [3, 2] | ≤0.3 |
| Volume weighted mean D [4, 3] | ≤0.3 |
| % Droplets >5 micrometer | ≤0.05 |

Further compositions prepared are given in Table 2. For some of these compositions, no stable emulsion could be obtained. Surprisingly, in particular emulsions comprising a combination of sodium oleate and lecithin turned out to be particularly stable.

The invention claimed is:

1. A composition comprising
   an aqueous phase and 5 to 30% by weight of an oil phase, based on the total weight of the composition, wherein the oil phase comprises eicosapentaenoic acid ethylester, docosahexaenoic acid ethylester or mixtures thereof and less than 1% by weight medium chain triglycerides, based on the total weight of the composition;
   an anionic surfactant; and
   an amphoteric surfactant, wherein the composition is formulated for parenteral administration and comprises less than 0.05% by weight of oleic acid, based on the total weight of the composition.

2. The composition of claim 1, wherein at least 60% by weight of the oil phase consists of eicosapentaenoic acid ethylester, docosahexaenoic acid ethylester or mixtures thereof.

3. The composition of claim 1, wherein the oil phase comprises a mixture of eicosapentaenoic acid ethylester and docosahexaenoic acid ethylester and wherein the weight ratio of the eicosapentaenoic acid ethylester to the docosahexaenoic acid ethylester is in the range of from 1 to 9 to 9 to 1.

4. The composition of claim 1, further comprising an agent with antioxidant activity.

5. The composition of claim 1, wherein the amphoteric surfactant is lecithin.

6. The composition of claim 1, wherein the anionic surfactant is sodium oleate.

7. The composition of claim 1, wherein the composition further comprises a tonicity agent.

| | Composition | | | | | | | | | |
|---|---|---|---|---|---|---|---|---|---|---|
| | 1 a, b, c | 2 a, b, c | 3 a, b, c | 4 a, b, c | 5 a, b, c | 6 a, b, c | 7 a, b, c | 8 a, b, c | 9 a, b, c | 10 a, b, c |
| DHA/EPA [weight.-%] | 20 Mixtures 1, 2, 3 | 20 Mixtures 1, 2, 3 | 20 Mixtures 1, 2, 3 | 20 Mixtures 1, 2, 3 | 20 Mixtures 1, 2, 3 | 20 Mixtures 1, 2, 3 | 20 Mixtures 1, 2, 3 | 20 Mixtures 1, 2, 3 | 20 Mixtures 1, 2, 3 | 20 Mixtures 1, 2, 3 |
| Egg lecithin [weight.-%] | 1.2 | 1.2 | 1.2 | 1.2 | 1.2 | 1.2 | 1.2 | 1.2 | 1.2 | 1.2 |
| Glycerol [weight.-%] | 2.5 | 2.5 | 2.5 | 2.5 | 2.5 | 2.5 | 2.5 | 2.5 | 2.5 | 2.5 |
| Tocopherols [weight.-%] | 0.02 | 0.02 | 0.02 | 0.02 | 0.02 | 0.02 | 0.02 | 0.02 | 0.02 | 0.02 |
| Oleic Acid [weight.-%] | — | — | — | — | 0.12 | 0.12 | 0.05 | 0.15 | 0.25 | 0.15 |
| Sodium Oleate [weight.-%] | 0.3 | 0.2 | 0.15 | 0.1 | 0.18 | 0.03 | 0.2 | — | — | — |
| PEG 400 [weight.-%] | — | — | — | — | — | — | — | 2 | 1 | — |
| Propylene glycol [weight.-%] | — | — | — | — | — | — | — | — | — | 1 |
| Water for injection | Adds up to 100 | Adds up to 100 | Adds up to 100 | Adds up to 100 | Adds up to 100 | Adds up to 100 | Adds up to 100 | Adds up to 100 | Adds up to 100 | Adds up to 100 |
| Stable Emulsion Y = yes; N = no | Y | Y | Y | Y | N spontaneously | N spontaneously | N spontaneously | N After some weeks | N After some weeks | N After some weeks |
| pH release | 8-9 | 8-9 | 8-9 | 8-9 | 8-9 | 8-9 | 8-9 | 8-9 | 8-9 | 8-9 |
| Surface mean droplet diameter D [3,2] | ≤0.3 | ≤0.3 | ≤0.3 | ≤0.3 | >0.3 | >0.3 | >0.3 | ≤0.3 | ≤0.3 | ≤0.3 |
| Volume weighted mean diameter D [4,3] | ≤0.3 | ≤0.3 | ≤0.3 | ≤0.3 | >0.3 | >0.3 | >0.3 | ≤0.3 | ≤0.3 | ≤0.3 |
| % Droplets >5 micrometer | ≤0.05 | ≤0.05 | ≤0.05 | ≤0.05 | >0.05 | >0.05 | >0.05 | >0.05 | >0.05 | >0.05 |

8. The composition of claim 1, wherein the composition comprises in sum less than 1% by weigh of polyethylene glycol and propylene glycol, based on the total weight of the composition.

9. The composition of claim 1, wherein the composition comprises less than 0.01% by weight oleic acid.

10. A method for preparing a composition, wherein the method comprises:
   (a) providing an aqueous phase comprising an amphoteric surfactant and an anionic surfactant,
   (b) providing an oil phase comprising eicosapentaenoic acid ethylester, docosahexaenoic acid ethylester or mixtures thereof, and
   (c) mixing the oil phase according to (b) with the aqueous phase according to (a), wherein the oil phase constitutes 5 to 30% by weight of the total composition, and the composition comprises less than 1% by weight medium chain triglycerides and less than 0.05% by weight oleic acid.

11. The method of claim 10, further comprising
   (d) homogenizing the mixture obtained from step (c) at a temperature in the range of from 50 to 60° C. and at a pressure in the range of from 450 to 550 bar.

12. The method of claim 11, further comprising
   (e) autoclaving the mixture obtained from step (c) or step (d) at a temperature in the range of from 119° C. to 122° C. for a time in the range of from 10 min to 15 min.

13. A composition obtained by the method of claim 10.

14. A method of providing parenteral nutrition to a patient suffering from stroke, sepsis, Alzheimer's disease or cancer, the method comprising parenterally administering to the patient an effective amount of the composition of claim 1.

15. An infusion bag comprising the composition of claim 1.

16. The composition of claim 4, wherein the agent with antioxidant activity is alpha-tocopherol, beta-tocopherol, gamma-tocopherol, ascorbic acid, ascorbic acid palmitate, or an antioxidant obtained or obtainable from rosemary or rosemary extract.

17. The composition of claim 7, wherein the tonicity agent is glycerol.

* * * * *